US007888400B2

(12) United States Patent
Abuelyaman et al.

(10) Patent No.: US 7,888,400 B2
(45) Date of Patent: Feb. 15, 2011

(54) DENTAL COMPOSITIONS CONTAINING HYBRID MONOMERS

(75) Inventors: Ahmed S. Abuelyaman, Woodbury, MN (US); Sumita B. Mitra, West St. Paul, MN (US); Kevin M. Lewandowski, Inver Grove Heights, MN (US); David J. Plaut, Minneapolis, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 602 days.

(21) Appl. No.: 11/912,949

(22) PCT Filed: May 9, 2006

(86) PCT No.: PCT/US2006/017833

§ 371 (c)(1),
(2), (4) Date: Apr. 2, 2008

(87) PCT Pub. No.: WO2006/122081

PCT Pub. Date: Nov. 16, 2006

(65) Prior Publication Data

US 2008/0194722 A1 Aug. 14, 2008

Related U.S. Application Data

(60) Provisional application No. 60/678,986, filed on May 9, 2005.

(51) Int. Cl.
*C08F 2/50* (2006.01)
*C08J 3/28* (2006.01)
*C07D 339/02* (2006.01)
*C07D 337/02* (2006.01)
*C07D 335/02* (2006.01)

(52) U.S. Cl. .................. 522/168; 522/71; 522/100; 522/113; 522/114; 522/118; 522/120; 522/122; 522/150; 522/153; 522/154; 522/167; 522/101; 522/178; 522/180; 522/181; 522/182; 523/105; 523/109; 523/113; 523/114; 523/115; 523/116; 523/118; 523/120; 523/300; 549/11

(58) Field of Classification Search .................. 522/71, 522/100, 101, 113, 114, 118, 120, 122, 150, 522/153, 154, 167, 168, 178, 180, 181, 182; 523/105, 109, 113, 114, 115, 116, 118, 120, 523/300; 549/11
See application file for complete search history.

(56) References Cited

U.S. PATENT DOCUMENTS

| 4,259,075 A | 3/1981 | Yamauchi et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,642,126 A | 2/1987 | Zador et al. |
| 4,648,843 A | 3/1987 | Mitra |
| 4,652,274 A | 3/1987 | Boettcher et al. |
| 4,665,217 A | 5/1987 | Reiners et al. |
| 4,695,251 A | 9/1987 | Randklev |
| 4,710,523 A | 12/1987 | Lechtken et al. |
| 4,737,593 A | 4/1988 | Ellrich et al. |
| 4,752,338 A | 6/1988 | Reiners et al. |
| 4,872,936 A | 10/1989 | Engelbrecht |
| 5,076,844 A | 12/1991 | Fock et al. |
| 5,130,347 A | 7/1992 | Mitra |
| 5,154,762 A | 10/1992 | Mitra et al. |
| 5,501,727 A | 3/1996 | Wang et al. |
| 5,530,038 A | 6/1996 | Yamamoto et al. |
| 5,545,676 A | 8/1996 | Palazzotto et al. |
| 5,670,657 A * | 9/1997 | Kojima et al. .......... 549/39 |
| 6,030,606 A | 2/2000 | Holmes |
| 6,043,361 A * | 3/2000 | Evans et al. ........... 544/1 |
| 6,251,963 B1 | 6/2001 | Kohler et al. |
| 6,307,062 B1 * | 10/2001 | Caye et al. ........... 549/11 |
| 6,344,556 B1 * | 2/2002 | Evans et al. .......... 540/467 |
| 6,387,981 B1 | 5/2002 | Zhang et al. |

(Continued)

FOREIGN PATENT DOCUMENTS

| EP | 0 173 567 | 8/1985 |
| EP | 0 373 384 | 6/1990 |
| EP | 0 712 622 | 9/1999 |
| EP | 1 051 961 | 2/2006 |
| WO | WO 94/14792 | 7/1994 |
| WO | WO 96/19471 | 6/1996 |
| WO | WO 00/38619 | 7/2000 |
| WO | WO 00/42092 | 7/2000 |
| WO | WO 01/07444 | 2/2001 |
| WO | WO 01/30305 | 5/2001 |

(Continued)

OTHER PUBLICATIONS

Moszner et al. New Developments of polymeric dental composites. Progress in Polymer Science, vol. 26, Issue 4, May 2001, pp. 535-576.*

(Continued)

*Primary Examiner*—Sanza L McClendon
(74) *Attorney, Agent, or Firm*—Stephen L. Crooks

(57) ABSTRACT

The invention features dental compositions comprising at least one hybrid monomer that comprises a cyclic allylic sulfide moiety attached to a (meth)acryloyl moiety. These two functional moieties are typically joined either directly to each via a chemical bond or through some chemical structure or spacer molecule. The composition may optionally contain additional polymerizable compounds, such as ethylenically unsaturated compounds, that are typically used in dental compositions.

20 Claims, No Drawings

U.S. PATENT DOCUMENTS

| | | |
|---|---|---|
| 6,458,868 B1 | 10/2002 | Okada et al. |
| 6,472,488 B2 * | 10/2002 | Caye et al. ............... 526/286 |
| 6,495,643 B1 * | 12/2002 | Evans et al. ............... 526/256 |
| 6,572,693 B1 | 6/2003 | Wu et al. |
| 6,669,927 B2 | 12/2003 | Trom et al. |
| 6,713,555 B2 * | 3/2004 | Moszner et al. ............ 524/588 |
| 6,765,036 B2 | 7/2004 | Dede et al. |
| 6,794,471 B2 * | 9/2004 | Ohkuma et al. ............ 526/256 |
| 7,090,721 B2 | 8/2006 | Craig et al. |
| 7,090,722 B2 | 8/2006 | Budd et al. |
| 7,156,911 B2 | 1/2007 | Kangas et al. |
| 7,495,054 B2 * | 2/2009 | Lewandowski et al. ..... 524/556 |
| 7,501,457 B2 * | 3/2009 | Angermann et al. ........ 523/116 |
| 2003/0060535 A1 | 3/2003 | Moszner et al. |
| 2003/0166740 A1 | 9/2003 | Mitra et al. |
| 2003/0195273 A1 | 10/2003 | Mitra et al. |
| 2004/0151691 A1 | 8/2004 | Oxman et al. |
| 2004/0206932 A1 | 10/2004 | Abuelyaman |
| 2005/0256223 A1 | 11/2005 | Kolb et al. |
| 2007/0066748 A1 * | 3/2007 | Lewandowski et al. ..... 524/556 |
| 2007/0203256 A1 * | 8/2007 | Angermann et al. ........ 523/116 |
| 2007/0248927 A1 | 10/2007 | Luchterhandt et al. |

FOREIGN PATENT DOCUMENTS

| | | |
|---|---|---|
| WO | WO 01/30306 | 5/2001 |
| WO | WO 01/30307 | 5/2001 |
| WO | WO 01/92271 | 12/2001 |
| WO | WO 03/063804 | 8/2003 |
| WO | WO 2006/122074 | 11/2006 |

OTHER PUBLICATIONS

Evans et al., "Free-Radical Ring-Opening Polymerization of Cyclic Allylic Sulfides: Liquid Monomers with Low Polymerization Volume Shrinkage," Journal of Polymer Science: Part A: Polymer Chemistry, 39, pp. 202-215, (2001).

Evans et al., "Free-Radical Ring-Opening Polymerization of Cyclic Allylic Sulfides," Macromolecules, 29, pp. 6983-6989, (1996).

Evans et al., "Free-Radical Ring-Opening Polymerization of Cyclic Allylic Sulfides. 2. Effect of Substituents on Seven- and Eight-Membered Ring Low Shrink Monomers," Macromolecules, 33, pp. 6722-6731, (2000).

Evans et al., "New Free-Radical Ring-Opening Acrylate Monomers," Macromolecules, 27, pp. 7935-7937, (1994).

Harrisson et al., "Pulsed Laser Copolymerization of Ring-Opening Cyclic Allylic Sulfife Monomers with Methyl Methacrylate and Styrene" Macromolecules, 35, pp. 2474-2480, (2002).

Watts et al., "Determination of Polymerization Shrinkage Kinetics in Visible-Light-Cured Materials: Methods Development," Dental Materials, pp. 281-287, (1991).

* cited by examiner

DENTAL COMPOSITIONS CONTAINING HYBRID MONOMERS

CROSS REFERENCE TO RELATED APPLICATIONS

This application is a national stage filing under 35 U.S.C. 371 of PCT/US2006/017833, filed May 9, 2006, which claims priority to U.S. Provisional Application No. 60/678,986, filed May 9, 2005, the disclosures of which are incorporated by reference in their entirety herein.

FIELD OF THE INVENTION

The present invention is generally related to hardenable dental compositions useful in restorative dentistry. More specifically, the invention relates to hardenable dental compositions containing free radical ring-opening cyclic allylic sulfide monomers that exhibit low polymerization shrinkage.

BACKGROUND

Dental composites made from organic resins and fillers are finding increasing use in dental applications, especially in restorative dentistry, due to their excellent aesthetic properties. Typical dental composite resins contain low viscosity di(meth)acrylate monomers, which serve as diluents that facilitate high filler levels. These diluents usually are small molecular weight (meth)acrylates, such as triethyleneglycol dimethacrylate (TEGDMA), which shrink substantially upon polymerization due to their low molecular weight. Polymerization shrinkage can lead to a number of problems in dental applications. For example, it often causes gaps between the composite and the tooth structure, which can lead to postoperative sensitivity, microleakage, enamel edge cracks, and secondary caries.

A number of factors are believed to play a role in polymerization shrinkage. It has been postulated that shrinkages occurs as the van der Waals distance between monomers are replaced by covalent bonds and the packing density of the polymers increases in comparison to that of the monomers. Recent efforts have been made to reduce polymeric shrinkage by attempting to minimize such phenomena; however, many of the low-shrink compositions currently available lack the physical, mechanical, and optical properties required for dental applications. Moreover, not all low-shrink compositions are efficiently polymerizable under conditions that are suitable for use in the oral cavity. Thus, despite substantial advancement in this area, polymerization shrinkage remains a significant problem when working with certain types of dental composites. Consequently, there remains a need for new composite materials that exhibit reduced polymeric shrinkage without sacrificing other beneficial properties, such as fracture toughness and aesthetics.

SUMMARY OF THE INVENTION

The present invention features a hardenable dental composition comprising a polymerizable compound having at least one cyclic allylic sulfide moiety and at least one (meth)acryloyl moiety. Such a polymerizable compound is referred to herein as a hybrid monomer or a hybrid compound. The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have to or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In some implementations, these hybrid monomers comprise an oxygen atom directly bonded to the ring structure of the cyclic allylic sulfide moiety. As used herein, "directly bonded to the ring structure" means that at least one of the carbon atoms of the ring is covalently bonded (typically the bond is a single bond) to an oxygen atom that is not one of the members of the ring, i.e. an oxygen that is not an atom in the ring itself. The extracyclic oxygen is typically not a member of any ring structure, but could be a member of a different ring.

In certain embodiments, the polymerizable compounds of the invention include those represented by the formulae:

Formula 1a

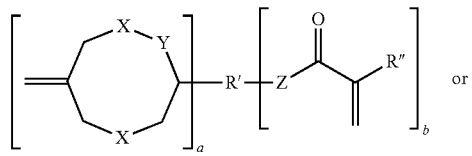

or

Formula 1b

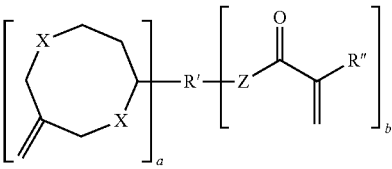

In the above formulae, each X can be independently selected from S, O, N, C (e.g., $CH_2$ or CRR, where each R is independently a H or an organic group), SO, $SO_2$, N-alkyl, N-acyl, NH, N-aryl, carboxyl or carbonyl group, provided that at least one X is S or a group comprising S. Preferably, each X is S.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively.

Z is O, NH, N-alkyl (straight chain or branched), or N-aryl (phenyl or substituted phenyl).

The R' group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

R" is selected from H, and $CH_3$, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical hybrid monomer of the present invention comprises an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The compositions of the invention may optionally include additional monomers, typically an ethylenically unsaturated compound. In one embodiment, the ethylenically unsaturated compound comprises a substituted (meth)acryl compound, such as, for example, a di(meth)acrylate, an aliphatic(meth)acrylate having at least one functional group, and/or a (meth)acrylate with an aromatic functionality. Examples of suitable substituted (meth)acryl compounds include, but are not limited to ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMA).

The compositions of the invention also typically comprise an initiator system, preferably a photoinitator system containing, for example, an acylphosphine oxide photoinitiator capable of absorbing light in the range of about 300 to about 600 nm and/or a tertiary photoinitiator system that includes an iodonium salt, an electron donor, and a photosensitizer.

The compositions optionally comprise one or more fillers of the sort typically used in dental materials that have been optionally treated with silanes containing free radically polymerizable functionalities.

The compositions of the invention are useful for a variety of dental treatments and restorative functions, including crown and bridge materials, fillings, adhesives, sealants, inlays, onlays, laminate veneers, luting agents or cements, denture base materials, orthodontic materials and sealants, and other dental restorative materials. The inclusion of a hybrid monomer comprising a cyclic allylic sulfide moiety and a (meth)acryl moiety in the composition results in excellent polymerization to form a hardened dental composite with low shrinkage and high mechanical properties.

The above summary is not intended to describe each embodiment or every implementation of the invention. Other embodiments, features, and advantages of the present invention will be apparent from the following detailed description thereof, and from the claims.

Definitions

As used herein, a "hardenable" component refers to one that is capable of polymerization and/or crosslinking reactions including, for example, photopolymerization reactions and chemical polymerization techniques (e.g., ionic reactions or chemical reactions forming radicals effective to polymerize ethylenically unsaturated compounds, (meth)acrylate compounds, etc.) involving one or more compounds capable of hardening. Hardening reactions also include acid-base setting reactions such as those common for cement forming compositions (e.g., zinc polycarboxylate cements, glass-ionomer cements, etc.).

As used herein, "dental composition" refers to hardenable compositions used in the oral environment including, for example, dental adhesives, orthodontic adhesives, composites, restoratives, dental cements, orthodontic cements, sealants, coatings, impression materials, filling materials, and combinations thereof. In some embodiments, dental compositions of the present invention including a hardenable component can be hardened to fabricate a dental article selected from the group consisting of crowns, bridges, veneers, inlays, onlays, fillings, mill blanks, impression materials, orthodontic devices, prostheses (e.g., partial or full dentures), and finishing or polishing devices as used for dental prophylaxis or restorative treatments (e.g., prophy agents such as cups, brushes, polishing agents).

As used herein, a "dental adhesive" refers to a non-filled or a lightly filled dental composition (e.g., less than 40% by weight filler), which is typically used to adhere a curable dental material (e.g., a filling material) to a tooth surface. After hardening, the dental compositions are typically not tacky or sticky and therefore would not be in the class of materials known as pressure sensitive adhesives (PSAs).

As used herein, "(meth)acryl" is a shorthand term referring to "acryl" and/or "methacryl." For example, a "(meth)acryloyloxy" group is a shorthand term referring to either an acryloyloxy group (i.e., $CH_2$=$CHC(O)O$—) and/or a methacryloyloxy group (i.e., $CH_2$=$C(CH_3)C(O)O$—); and a "(meth)acryloyl" group is a shorthand term referring to either an acryloyl group (i.e., $CH_2$=$CHC(O)$—) and/or a methacryloyl group (i.e., $CH_2$=$C(CH_3)C(O)$—).

By "substituted (meth)acryloyl compound" is meant a (meth)acryloyl compound, such as a (meth)acrylate, having an organic substituent other than methyl on the oxygen.

By "photosensitizer" is meant any substance that either increases the rate of photo-initiated polymerization or shifts the wavelength at which polymerization occurs. Typical photosensitizers are monoketones and diketones that absorb some light within a range of 400 nm to 520 nm.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The present invention provides hardenable dental compositions that have low polymerization shrinkage and high mechanical properties that are useful in dental restorative applications. These compositions contain at least one hybrid monomer that comprises a cyclic allylic sulfide moiety chemically attached to a (meth)acryl moiety. These two functional entities are typically joined either directly to each other via a chemical bond or through some chemical structure or spacer (i.e., linker) molecule. The composition may optionally contain additional polymerizable compounds, such as ethylenically unsaturated compounds typically used in dental compositions, for example a substituted (meth)acrylate or similar compound.

In one embodiment, the compositions further include a initiator system, typically a photoinitiator system, which upon irradiation with actinic radiation of the appropriate wavelength, initiates the polymerization (or hardening) of the composition. The compositions can be hardened (e.g., polymerized by conventional photopolymerization and/or chemical polymerization techniques) prior to or after applying or after the dental material. Fillers and other optional additives may also be incorporated into the composition.

Hybrid Monomer Component

The hybrid monomers of the present invention can be made from hydroxy-substituted cyclic allylic sulfide compounds, including certain of those described in U.S. Pat. No. 6,495,643 (Evans et al.); U.S. Pat. No. 6,344,556 (Evans et al.); U.S. Pat. No. 6,043,361 (Evans et al.); WO 96/19471 (Evans et al.); WO 94/14792 (Rizzardo et al.); Richard Evans et al, *New Free-Radical Ring-Opening Acrylate Monomers*, Macromolecules, 1994, 27 (26), 7935-7937; Richard Evans and Ezio Rizzardo, *Free-Radical Ring-Opening Polymerization of Cyclic Allylic Sulfides*, Marcomolecules, 1996, 29, 6983-6989; Richard Evans and Ezio Rizzardo, *Free Radical Ring-Opening Polymerization of Cyclic Allylic Sulfides. 2. Effect of Substituents on Seven- and Eight-Membered Ring Low Shrink Monomers*, Macromolecules, 2000, 33, 6722-6731, and Richard Evans and Ezio Rizzardo, *Free Radical Ring-Opening Polymerization of Cyclic Allylic Sulfides: Liquid Monomers with Low Polymerization Volume Shrinkage*, Journal of Polymer Science: Part A: Polymer Chemistry, 2001, 39, 202-215, all of which are hereby incorporated by reference herein in their entirety.

The hybrid monomers of the invention can be created by attaching one or more (meth)acryloyl moieties to one or more of these hydroxy-substituted cyclic allylic sulfide compounds. Preferred hydroxy-substituted cyclic allylic sulfide compounds include C-8 Alcohol (7-methylene-1,5-dithiacyclooctan-3-ol; described in the Examples Section), C-8 Methanol (7-methylene-1,5-dithiacyclooctan-3-methanol), C-7 Alcohol (6-methylene-1,4-dithiacycloheptan-3-ol), and C-7 Methanol (6-methylene-1,4-dithiacycloheptan-3-methanol; described as Compound 1a-4 in U.S. Pat. No. 6,495,643 (Evans et al.). Typically, the hybrid monomers of the present invention can be obtained by reacting a hydroxy-substituted cyclic allylic sulfide compound with an organic molecule having at least one (meth)acryloyl moiety and at least one group reactive with a hydroxy group (e.g., an acid group, acid halide group, anhydride group, or isocyanate group). The reaction of the hydroxy-reactive group of the organic molecule with the hydroxy-substituted cyclic allylic sulfide compound can lead to specific hybrid monomers of the invention. Thus, for example, C-8 Alcohol can be reacted with mono-2-methacryloyloxyethyl phthalate to afford the hybrid monomer 1-(2-methacryloyloxyethyl)-2-(7-methylene-1,5-dithiaoctan-3-yl) phthalate (Example 1; Compound A). Alternatively, a cyclic allylic sulfide compound could be substituted with a group reactive with a hydroxy group (e.g., an acid group, acid halide group, anhydride group, or isocyanate group) and reacted with a hydroxy-substituted methacrylate (e.g., HEMA) to afford a variety of hybrid monomers. These synthetic routes represent only some of the many possible organic synthetic methods to the hybrid monomers of the invention. Such methods would be readily known to one of skill in the art.

In one embodiment, the cyclic allylic sulfide moieties comprise a ring structure having 7 to 8 members that has at least one heteroatom, typically a sulfur atom, which may optionally be present as part of an SO, $SO_2$, or S—S moiety. Most typically, the rings comprise two sulfur atoms, or a sulfur atom plus a second, different heteroatom, such as oxygen or nitrogen, in the ring. In addition, the cyclic allylic sulfide moiety may comprise multiple ring structures and therefore the hybrid monomer may have two or more cyclic allylic sulfide moieties.

Representative examples of the compounds of the invention are as follows:

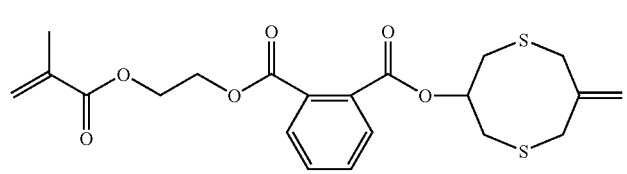

1a-1

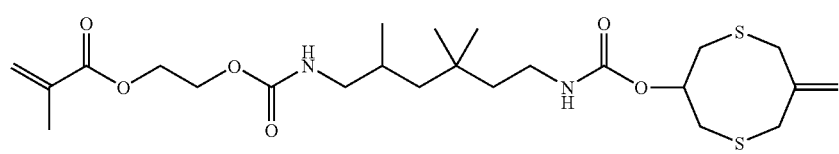

1a-2

-continued

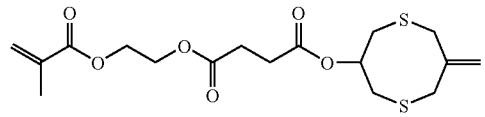
1a-3

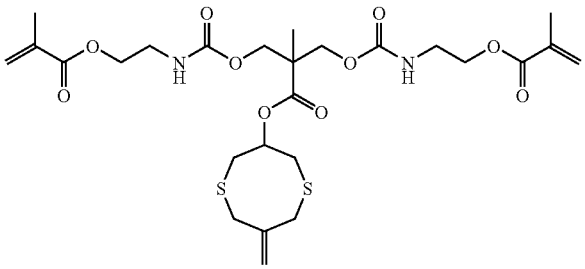
1a-4

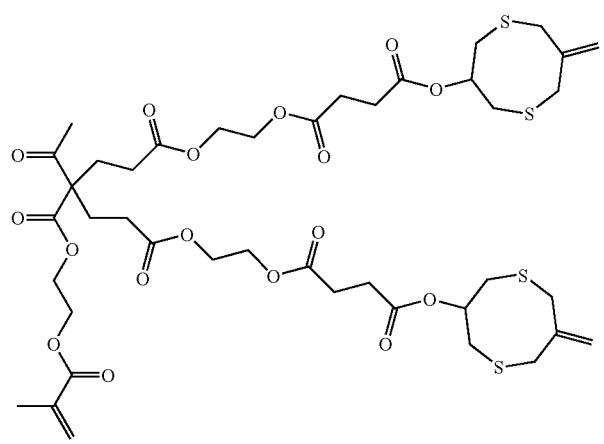
1a-5

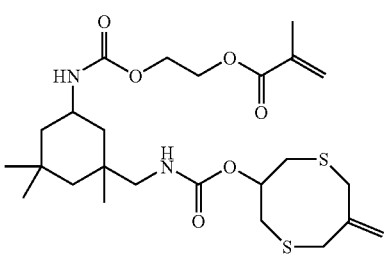
1a-6

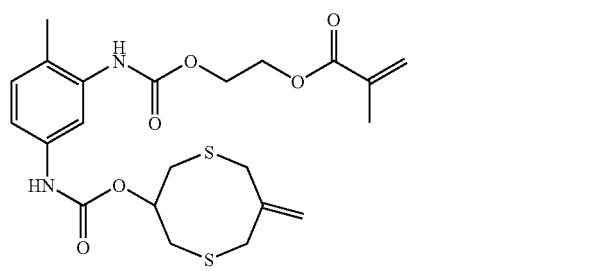
1a-7

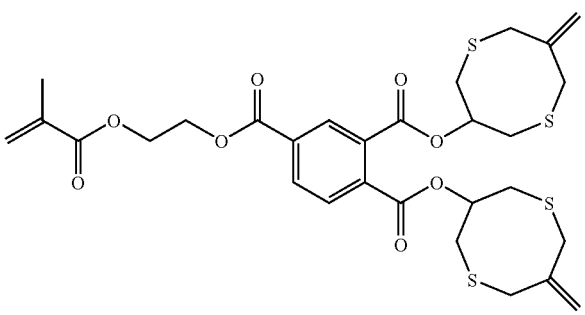
1a-8

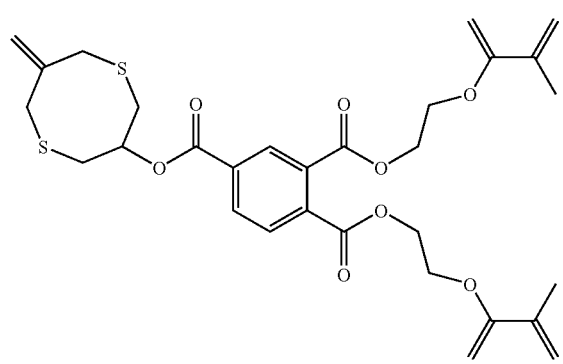
1a-9

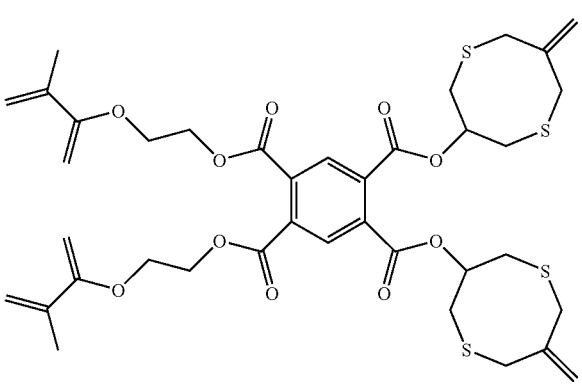
1a-10

Ethylenically Unsaturated Component

The compositions of the present invention may also include one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, acrylamides, methacrylamides, and combinations thereof.

The compositions (e.g., photopolymerizable compositions) may include compounds having free radically active functional groups that may include monomers, oligomers, and polymers having one or more ethylenically unsaturatd group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloyloxy)]-p-ethoxyphenyldimethylmethane, bis[1-(3-acryloyloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The ethylenically unsaturated compound may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

In certain embodiments, the ethylenically unsaturated compound preferably comprises a substituted (meth)acryl compound. Particularly useful (meth)acryl compounds include di(meth)acrylates, aliphatic (meth)acrylates having at least one functional group, and (meth)acrylates with an aromatic functionality. Examples of suitable substituted (meth)acryl compounds include ethoxylated bisphenol A dimethacrylate (BisEMA6) as described in U.S. Pat. No. 6,030,606 (Holmes), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMA). Various combinations of these compounds can be used if desired.

Typically, compositions of the present invention include at least 5% by weight, more typically at least 10% by weight, and most typically at least 15% by weight ethylenically unsaturated compounds, based on the total weight of the unfilled composition. Typically, compositions of the present invention include at most 95% by weight, more typically at most 90% by weight, and most typically at most 80% by weight ethylenically unsaturated compounds, based on the total weight of the unfilled composition.

Typically, compositions of the present invention include at least 5% by weight (wt-%), more typically at least 10% by weight, and most typically at least 15% by weight ethylenically unsaturated compounds without acid functionality, based on the total weight of the unfilled composition. Typically, compositions of the present invention include at most 95% by weight, more typically at most 90% by weight, and most typically at most 80% by weight ethylenically unsaturated compounds without acid functionality, based on the total weight of the unfilled composition.

Ethylenically Unsaturated Compounds with Acid Functionality

Generally, the composition of the invention include ethylenically unsaturated compounds without acid functionality; however, in some embodiments of the invention the compositions may instead, or in addition, include one or more ethylenically unsaturated compounds with acid functionality.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include oxyacids of C, B, P or S or combinations thereof. Examples include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloyloxyethyl) phosphate, ((meth)acryloyloxypropyl) phosphate, bis((meth)acryloyloxypropyl) phosphate, bis((meth)acryloyloxy)propyloxy phosphate, (meth)acryloyloxyhexyl phosphate, bis((meth)acryloyloxyhexyl) phosphate, (meth)acryloyloxyoctyl phosphate, bis((meth)acryloyloxyoctyl) phosphate, (meth)acryloyloxydecyl phosphate, bis((meth)acryloyloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include compositions that include combinations of ethylenically unsaturated compounds with acid functionality. Typically the compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth) acryloxy group are linked together by a C1-C4 hydrocarbon group; a second compound including at least one (meth) acryloxy group and at least one —O—P(O)(OH)$_x$ group, wherein x=1 or 2, and wherein the at least one —O—P(O) (OH)$_x$ group and the at least one (meth)acryloxy group are linked together by a C5-C12 hydrocarbon group; an ethylenically unsaturated compound without acid functionality; an initiator system; and a filler. Such compositions are described, for example, in U.S. Provisional Application Ser. No. 60/600,658 (Luchterhandt et al.), filed on Aug. 11, 2004.

Typically, the compositions of the present invention include at least 1% by weight, more typically at least 3% by weight, and most typically at least 5% by weight ethylenically unsaturated compounds with acid functionality, based on the total weight of the unfilled composition. Typically, compositions of the present invention include at most 80% by weight, more typically at most 70% by weight, and most typically at most 60% by weight ethylenically unsaturated compounds with acid functionality, based on the total weight of the unfilled composition.

Photoinitiator System

In certain embodiments, the compositions of the present invention are photopolymerizable, i.e., the compositions contain a photopolymerizable component and a photoinitiator (i.e., a photoinitiator system) that upon irradiation with actinic radiation initiates the free radical polymerization (or hardening) of the composition. Suitable photoinitiators for polymerizing free radically photopolymerizable compositions include the class of phosphine oxides that typically have a functional wavelength range of 300 nm to 1200 nm, more typically in the range of 300 nm to 600 nm. Especially useful phosphine oxide free radical initiators, which generally have a functional wavelength range of 380 nm to 450 nm, are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), bis(.eta.5-2-4-cyclopentadien-1-yl)-bis(2,6-difluoro-3-(1H-pyrrol-1yl)-phenyl)titanium (IRGACURE 784, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Other suitable photoinitiators (i.e., photoinitiator systems that include one or more compounds) for polymerizing free radically photopolymerizable compositions include binary and tertiary systems. Typical tertiary photoinitiator systems include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 in (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.). Still other suitable initiator systems are described in pending U.S. Provisional Application No. 60/679265 entitled Hardenable Dental Compositions with Low Polymerization Shrinkage.

The compositions of the invention typically contain at least 0.03 wt-%, more typically at least 0.08 wt-%, even more typically at least 0.12 wt-%, and most typically at least 0.18 wt-% of a photosensitizer, based on the total weight of the composition.

The photoinitiator system is present in an amount sufficient to provide the desired rate of hardening (e.g., polymerizing and/or crosslinking). The amounts of photoinitiator system components in a composition will be dependent in part on the light source, the thickness of the layer to be exposed to radiant energy, and the extinction coefficient of the component(s).

Redox Initiator System

In some embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements, resin-modified glass ionomer cements, redox cure systems, and combinations thereof.

The chemically hardenable compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 5,154,762 (Mitra et al.), and U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline and N,N-bis(hydroxyethyl-p-toluidine; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydropemxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the hardenable composition except for the optional filler, and observing whether or not a hardened mass is obtained.

Typically, the reducing agent is present in an amount of at least 0.01% by weight, and more typically at least 0.1% by weight, based on the total weight (including water) of the components of the hardenable composition. Typically, the reducing agent is present in an amount of no greater than 10% by weight, and more typically no greater than 5% by weight, based on the total weight (including water) of the components of the hardenable composition.

Typically, the oxidizing agent is present in an amount of at least 0.01% by weight, and typically at least 0.10% by weight, based on the total weight (including water) of the components of the hardenable composition. Typically, the oxidizing agent is present in an amount of no greater than 10% by weight, and more typically no greater than 5% by weight, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state. A redox cure system can be combined with other cure systems, e.g., with a hardenable composition such as described U.S. Pat. No. 5,154,762 (Mitra et al.).

Fillers

The compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Typically, the maximum particle size (the largest dimension of a particle, typically, the diameter) of the filler is less than 20 micrometers, more typically less than 10 micrometers, and most typically less than 5 micrometers. Typically, the average particle size of the filler is less than 0.4 micrometers, more typically less than 0.1 micrometers, and most typically less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. Any coupling agent with a group that is co-polymerizable with the monomers of this invention would be suitable. The coupling agent could optionally contain a cyclic allylic sulfide unit. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include non-aggregated nanosized silica particles, non-aggregated nanosized metal oxide particles, clusters of nanosized particles, and combinations thereof. Nanofillers are also described in U.S. patent application Ser. No. 10/847,781 (Kangas et al.); Ser. No. 10/847,782 (Kolb et al.); Ser. No. 10/847,803 (Craig et al.); and Ser. No. 10/847,805 (Budd et al.) all four of which were filed on May 17, 2004. These applications, in summary, describe the following nanofiller containing compositions: U.S. patent application Ser. No. 10/847,781 (Kangas et al.) describes stable ionomer compositions (e.g., glass ionomer) containing nanofillers that provide the compositions with improved properties over previous ionomer compositions. In one embodiment, the composition is a hardenable dental composition comprising a polyacid (e.g., a polymer having a plurality of acidic repeating groups); an acid-reactive filler; at least 10 percent by weight nanofiller or a combination of nanofillers each having an average particle size no more than 200 nanometers; water; and optionally a polymerizable component (e.g., an ethylenically unsaturated compound, optionally with acid functionality).

U.S. patent application Ser. No. 10/847,782 (Kolb et al.) describes stable ionomer (e.g., glass ionomer) compositions containing nanozirconia fillers that provide the compositions with improved properties, such as ionomer systems that are optically translucent and radiopaque. The nanozirconia is surface modified with silanes to aid in the incorporation of the nanozirconia into ionomer compositions, which generally contain a polyacid that might otherwise interact with the nanozirconia causing coagulation or aggregation resulting in undesired visual opacity. In one aspect, the composition can be a hardenable dental composition including a polyacid; an acid-reactive filler; a nanozirconia filler having a plurality of silane-containing molecules attached onto the outer surface of the zirconia particles; water; and optionally a polymerizable component (e.g., an ethylenically unsaturated compound, optionally with acid functionality).

U.S. patent application Ser. No. 10/847,803 (Craig et al.) describes stable ionomer compositions (e.g., glass ionomers) containing nanofillers that provide the compositions with enhanced optical translucency. In one embodiment, the composition is a hardenable dental composition including a polyacid (e.g., a polymer having a plurality of acidic repeating groups); an acid-reactive filler; a nanofiller; an optional polymerizable component (e.g., an ethylenically unsaturated compound, optionally with acid functionality); and water. The refractive index of the combined mixture (measured in the hardened state or the unhardened state) of the polyacid, nanofiller, water and optional polymerizable component is generally within 4 percent of the refractive index of the acid-reactive filler, typically within 3 percent thereof, more typically within 1 percent thereof, and even more typically within 0.5 percent thereof.

U.S. patent application Ser. No. 10/847,805 (Budd et al.) describes dental compositions that can include an acid-reactive nanofiller (i.e., a nanostructured filler) and a hardenable resin (e.g., a polymerizable ethylenically unsaturated compound. The acid-reactive nanofiller can include an oxyfluoride material that is acid-reactive, non-fused, and includes a trivalent metal (e.g., alumina), oxygen, fluorine, an alkaline earth metal, and optionally silicon and/or a heavy metal.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., where the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water. If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. U.S. Pat. No. 6,669,927 (Trom et al.) and U.S. Pat. Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The hardenable dental compositions of the present invention can be prepared by combining a hybrid monomer with other optional components, such as one or more additional monomers, e.g., an ethylenically unsaturated component (e.g., a substituted (meth)acryl compound), using conventional mixing techniques. The resulting composition may optionally contain enhancers, surfactants, fillers, water, co-solvents, and other additives as described herein. In use, the compositions may contain a photoinitiator system and be hardened by photoinitiation, or may be hardened by chemical polymerization and contain a redox cure system in which the composition contains an oxidizing agent and a reducing agent. Alternatively, the hardenable composition may contain different initiator systems, such that the composition can be both a photopolymerizable and a chemically polymerizable composition.

The hardenable compositions of the invention can be supplied in a variety of forms including one-part systems and multi-part systems, e.g., two-part powder/liquid, paste/liquid, and paste/paste systems. Other forms employing multi-part combinations (i.e., combinations of two or more parts), each of which is in the form of a powder, liquid, gel, or paste are also possible. In a redox multi-part system, one part typically contains the oxidizing agent and another part typically contains the reducing agent. In multi-part systems containing an antimicrobial lipid component, one part typically contains the antimicrobial lipid component and another part contains either the hardenable component or other components of the final composition. The components of the hardenable composition can be included in a kit, where the contents of the composition are packaged to allow for storage of the components until they are needed. When used as a dental composition, the components of the hardenable compositions can be mixed and clinically applied using conventional techniques. A curing light is generally required for the initiation of photopolymerizable compositions. The compositions can be in the form of composites or restoratives that adhere very well to dentin and/or enamel. Optionally, a primer layer can be used on the tooth tissue on which the hardenable composition is used. The compositions, e.g., containing a FAS glass or other fluoride releasing material, can also provide very good long-term fluoride release. Some embodiments of the invention may provide glass ionomer cements or adhesives that can be cured in bulk without the application of light or other external curing energy, do not require a pre-treatment, have improved physical properties.

The compositions of the invention are particularly well adapted for use in the form of a wide variety of dental materials, which may be filled or unfilled. They can be used in sealants, coatings, or dental adhesives, which are lightly filled composites (up to 40 wt-% filler, based on the total weight of the composition) or unfilled compositions that are cured after being dispensed adjacent to a tooth (i.e., placing a dental material in temporary or permanent bonding or touching contact with a tooth). They can be used in dental and orthodontic cements, orthodontic adhesives, composites, filling materials, impression materials, and restoratives, which are typically filled compositions (preferably containing greater than 40 wt-% filler and up to 90 wt-% filler).

The compositions can also be used in prostheses that are shaped and polymerized for final use (e.g., as a crown, bridge, veneer, inlay, onlay, or the like), before being disposed adjacent to a tooth. Such preformed articles can be ground or otherwise formed into a custom-fitted shape by the dentist or other user. Although the hardened dental material can be any of a wide variety of materials that are prepared from hardenable components, preferably, the hardened dental material is not a surface pre-treatment material (e.g., etchant or primer). Rather, preferably, the hardened dental material is a restorative (e.g., filling or prosthesis), mill blank, or orthodontic device.

The compositions have utility in clinical applications where cure of conventional light-curable cement may be difficult to achieve. Such applications include, but are not limited to, deep restorations, large crown build-ups, endodontic restorations, attachment of orthodontic brackets (including pre-coated brackets, where, for example, a paste portion could be pre-applied to the bracket and a liquid portion could later be brushed onto a tooth), bands, buccal tubes, and other devices, luting of metallic crowns or other light-impermeable prosthetic devices to teeth, and other restorative applications in inaccessible areas of the mouth.

Typical compositions are used as dental adhesives, orthodontic adhesives, composites, restoratives, dental cements, orthodontic cements, sealants, coatings, impression materials, filling materials, or combinations thereof.

Further features and advantages of this invention are further illustrated by the following examples, which are in no way intended to be limiting thereof. The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification. Unless otherwise indicated, all parts and percentages provided in the examples are on a weight basis, all water is deionized water, and all molecular weights are weight average molecular weight.

EXAMPLES

Test Methods

Compressive Strength (CS) Test Method

Compressive strength of a test sample was measured according to the following procedure. An uncured composite sample was injected into a 4-mm (inside diameter) glass tube; the tube was capped with silicone rubber plugs; and then the tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). Cured samples were allowed to stand for 1 hour at about 37° C./90%+Relative Humidity and then were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Five cylinders of cured samples were prepared and measured with the results reported in MPa as the average of the five measurements.

Diametral Tensile Strength (DTS) Test Method

Diametral tensile strength of a test sample was measured as described for the CS Test Method, except that the cured samples were cut into 2.2-mm thick disks for measurement of DTS. The disks were stored in water and measured with an Instron tester as described above. Six disks of cured samples were prepared and measured with results reported in MPa as the average of the six measurements.

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample and were standardized to the performance of 3M FILTEK SUPREME Universal Restorative (3M Company).

Visual Opacity (MacBeth Values) Test Method

Disc-shaped (1-mm thick×15-mm diameter) paste samples were cured by exposing them to illumination from a VISILUX 2 curing light (3M Company) for 60 seconds on each side of the disk at a distance of 6 mm. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Barcol Hardness Test Method

Barcol Hardness of a test sample was measured according to the following procedure. An uncured composite sample was cured in 2.5-mm thick TEFLON mold sandwiched between a sheet of polyester (PET) film and a glass slide for 30 seconds with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure. Results were reported as the average of XXX (?) replicates for each sample and were standardized to the performance of 3M FILTEK SUPREME Universal Restorative (3M Company).

Abbreviations, Descriptions, and Sources of Materials

| Abbreviation | Description and Source of Material |
|---|---|
| BisEMA6 | Ethoxylated bisphenol A dimethacrylate (Sartomer, Exton, PA) |
| BisGMA | 2,2-Bis[4-(2-hydroxy-3-methacryloyloxypropoxy)phenyl]propane CAS No. 1565-94-2 |
| HEMA | 2-Hydroxyethyl methacrylate (Sigma-Aldrich, St. Louis, MO) |
| UDMA | Diurethane dimethacrylate (CAS No. 41137-60-4), commercially available as Rohamere 6661-0 (Rohm Tech, Inc., Malden, MA) |
| C-8 Alcohol | 7-Methylene-1,5-dithiacyclooctan-3-ol was prepared from 3-choro-2-(chloromethyl)-1-propene (Secant Chemicals Inc., Winchendon, MA) and 1,3-dibromo-2-propanol (Sigma-Aldrich) according to the procedure described in the following reference: R. Evans and E. Rizzardo, Free-Radical Ring-Opening Polymerization of Cyclic Allylic Sulfides. 2. Effect of Substituents on Seven- and Eight-Membered Ring Low Shrink Monomers, Macromolecules, 2000, 33, pp. 6722-6731. |

| Abbreviation | Description and Source of Material |
|---|---|
| C-8 Acetate | 7-Methylene-1,5-dithiacyclooctan-3-yl acetate was prepared from C-8 Alcohol and acetyl chloride (Alpha Aesar, Ward Hill, MA) according to the procedure described in the reference cited above for C-8 Alcohol. |

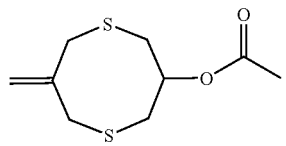

| | |
|---|---|
| C-8 Diurethane | 1,6-Bis(7-methylene-1,5-dithiacyclooctan-3-yl)-2,4,4-trimethylhexane dicarbamate (C-8 Diurethane) was prepared from C-8 Alcohol and 2,4,4-trimethyl-1,6-diisocyanatohexane (Sigma-Aldrich) according to the Preparatory Example 1 described herein. |

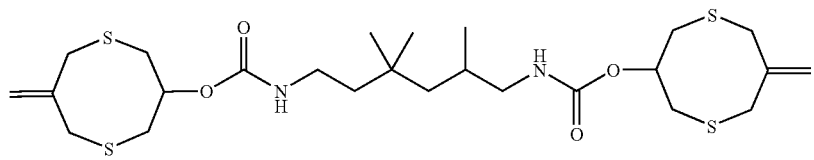

| | |
|---|---|
| IEM | 2-Isocyanoatoethyl methacrylate (Sigma-Aldrich) |
| CPQ | Camphorquinone (Sigma-Aldrich) |
| EDMAB | Ethyl 4-(N,N-dimethylamino)benzoate (Sigma-Aldrich) |
| DPIHFP | Diphenyl Iodonium Hexafluorophosphate (Alpha Aesar, Ward Hill, MA) |
| I-819 | IRGACURE 819 phosphine oxide photoinitiator (Ciba Specialty Chemicals Corp., Terrytown, NY) |
| BHT | 2,6-di-tert-butyl-4-methylphenol (Sigma-Aldrich) |
| Filler A | Silane-treated, nano-sized silica and zirconia particles loosely aggregated as substantially amorphous clusters were prepared in the form of a dry powder according to the procedure for Filler B in U.S. Pat. Publication No. 2003/0181541 (Wu et al.). |
| DMAP | 4-(N,N-Dimethylamino)pyridine (Sigma-Aldrich) |
| DCC | N,N-Dicyclohexyl carbodiimide (Alpha Aesar) |
| DBU | 1,8-Diazabicyclo[5.4.0]undec-7-ene (Lancaster Synthesis, Windham, NH) |

Preparatory Example 1

C-8 Diurethane (1,6-Bis(7-methylene-1,5-dithiacyclooctan-3-yl)-2,4,4-trimethylhexane dicarbamate)

7-Methylene-1,5-dithiacyclooctan-3-ol (C-8 Alcohol; 2.9 g, 16 mmole) and dibutyl tin dilaurate (10 mg; Sigma-Aldrich) were dissolved in dry tetrahydrofuran (THF, 10 ml) under nitrogen. The resulting solution was heated to reflux and a solution of 2,4,4-trimethyl-1,6-diisocyanatohexane (1.76 g, 8.2 mmole) in dry THF (10 ml) was added dropwise. The reaction was monitored by thin layer chromatography (ether:methylene chloride 1:1) until the starting C8-Alcohol was consumed. (About 12 hours reaction time.) The solvent was then evaporated to give a viscous clear oil/gum. The oil/gum was purified by dissolving in methanol (15 ml per gram) to give a slightly milky solution. A small quantity of the gum separated. The solution was filtered into another flask and water (3 ml per gram) was added slowly to the filtrate with stirring. During the addition, a white residual material separated from the solution. The liquid solvent was decanted and the residue was washed with methanol:water 3.5:1. The washed residue was dissolved in methylene chloride, BHT inhibitor was added (1 mg per gram), and the solution dried with sodium sulfate. The solvent was evaporated to give a slightly cloudy viscous liquid (4.36 g, 96% yield). The product structure of C-8 Diurethane was confirmed by 1H and 13C NMR.

Example 1

1-(2-Methacryloyloxyethyl)-2-(7-methylene-1,5-dithiaoctan-3-yl) Phthalate

Compound A mono-2-Methacryloyloxyethyl phthalate (9.4 g, 31 mmole, Sigma-Aldrich) and C-8 Alcohol (5.38 g, 31 mmole) were dissolved in methylene chloride (50 ml) in a 3-neck flask equipped with a magnetic stirring bar and nitrogen gas inlet. DMAP (400 mg) was added and the resulting mixture was cooled in an ice bath for 20 minutes. To the cooled solution was added a solution of DCC (6.95 g, 34 mmol) in methylene chloride (50 ml). The addition was carried out dropwise over 1 hour while the flask contents were continuously stirred under nitrogen at 0° C. The resulting mixture was then stirred with the flask in the ice bath for 1 hour and then at room temperature overnight. The resulting precipitate was removed by vacuum filtration using a Buchner funnel with filtration aid celite. The filtrate was then washed once with 0.1 N HCl (100 ml), once with 5% NaOH (100 ml), and once with water (100 ml). The organic layer was dried and concentrated to give a slightly cloudy viscous liquid (11.4 g; 84% yield). Purity and structure of Example 1 (Compound A) were confirmed by 13C and 1H NMR.

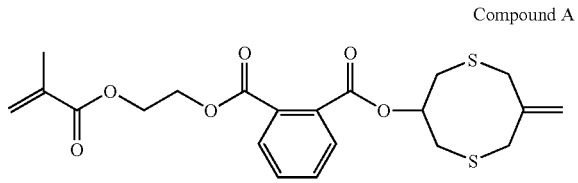

Compound A

Example 2

1-(Methacryloyloxyethyl)-6-(7-methylene-15-thiacy-clooctan-3-yl)-2,4,4-trimethylhexane Dicarbamate Compound B 2,4,4-Trimethyl-1,6-diisocyanatohexane (17.6 g, 84 mmol) was dissolved in methylene chloride (100 ml) in a 3-neck flask equipped with a stirring bar and nitrogen inlet. To the flask was added dibutyl tin dilaurate (10 drops, Sigma-Aldrich) and to the continuously stirring solution was further added C-8 Alcohol in small increments (total added: 14.8 g, 84 mmol). The resulting mixture was stirred at room temperature for 6 hours during which time all of the C-8 Alcohol disappeared as monitored by thin layer chromatography (4:1 hexane:ethyl acetate, silica gel on glass plates). HEMA (10.92 g, 84 mmole) was added dropwise to the mixture and the disappearance of the isocyanato moiety (—NCO) was monitored by FT (Fourier Transform) IR spectroscopy. Stirring was continued overnight, after which IR indicated about 95% NCO reaction completion. Methanol (10 ml) was added and after 0.5 hour, the NCO reaction was complete. The solvent was removed under vacuum to give Example 2 (Compound B) as a colorless viscous liquid. Yield was quantitative. Purity and structure were confirmed by 13C and 1H NMR.

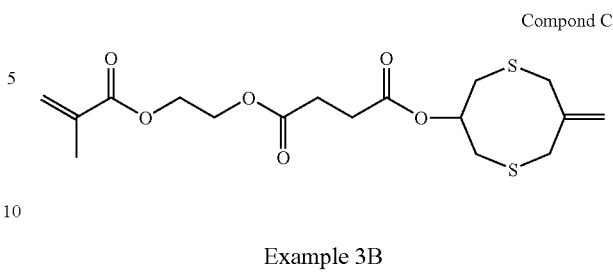

Compond C

Example 3B 1-(2-Acryloyloxyethyl)2-(7-methylene-1,5-dithiacy-clooctan-3-yl) Succinate Compound D Example 3B was prepared from the C-8 Alcohol and mono-2-acryloyloxyethyl succinate (Sigma-Aldrich) following the general procedure of esterification described for Example 1. Purity and structure verification of Example 3B (Compound D) were confirmed by 1H and 13C NMR.

Example 4A (7-Methylene-1,5-dithiacyclooctan-3-yl) 2,2-Bis (IEM-methyl)propionate Compound E 2,2-Bis(hydroxymethyl)propionic acid (15.0 g, 112 mmol, Sigma-Aldrich) was suspended in THF (100 ml) under nitrogen with continuous stirring using a magnetic stirring bar. Dibutyltin dilaurate (10 drops) was added followed by the addition of IEM (35.4 g, 112 mmol) dropwise to the vigorously stirred suspension at room temperature. The mixture was stirred overnight (the mixture became clear) and FTIR indicated that less than 5% of the —NCO moiety remained unreacted. Methanol (2 ml) was added and the mixture was

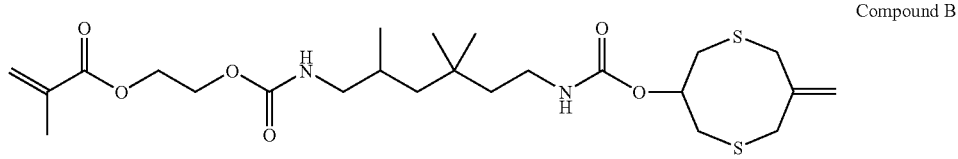

Compound B

Example 3A 1-(2-Methacryloyloxyethyl)-2-(7-methylene-1,5-dithiacyclooctan -3-yl) Succinate Compound C Example 3A was prepared from the C-8 Alcohol and mono-2-methacryloyloxyethyl succinate (Sigma-Aldrich) following the general procedure of esterification described for Example 1. Purity and structure verification of Example 3A (Compound C) were confirmed by 1H and 13C NMR.

stirred for 2 extra hours after which all of the —NCO had reacted. The solvent was removed in a rotary evaporator to give a clear viscous liquid (IEM adduct-propionic acid) in a quantitative yield.

The isolated IEM adduct-propionic acid was esterified with the C-8 Alcohol following the general procedure of esterification described for Example 1. A white wax solid was isolated. The structure of Example 4A (Compound E) was confirmed by 1H and 13C NMR. Because of its waxy nature, it was found to be very difficult to add significant amounts of a filler to Example 4A and no paste formulations were made of this compound.

Compound E

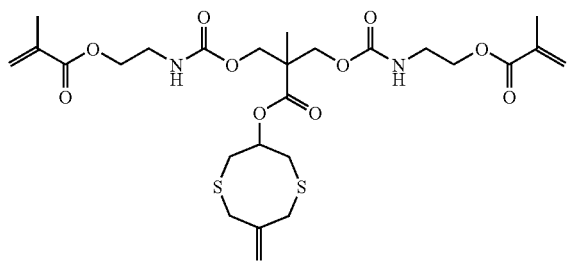

Example 4B

Reaction Product of 2-(Methacryloyloxy)ethyl acetoacetate and Example 3B

Compound F 1-(2-Acryloyloxyethyl)-2-(7-methylene-1,5-dithiaoctan-3-yl) succinate (Example 3B, 5.25 g, 0.0134 mol) was placed in a glass vial followed by 2 drops of DBU. The components were hand mixed for 30 seconds followed by the addition of 2-(methacryloyloxy)ethyl acetoacetate (1.35 g, 0.0068, Sigma-Aldrich) and subsequent hand mixing for one minute. The vial was remained at room temperature for 3 hours, during which time the product was formed as a colorless viscous liquid in a quantitative yield. The structure of Example 4B (Compound F) was confirmed by 1H and 13C NMR. Because of its highly viscous nature, it was found to be very difficult to add significant amounts of a filler to Example 4B and no paste formulations were made of this compound.

Compound F

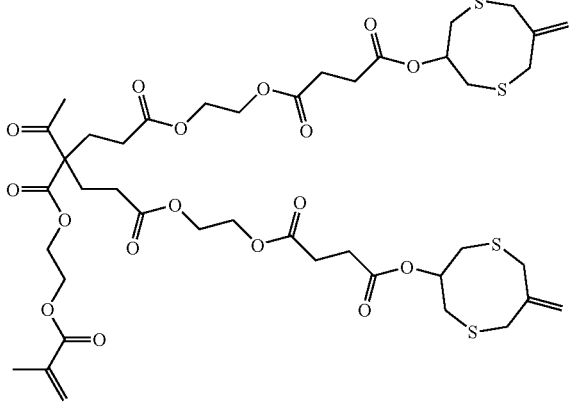

Examples 5-9 and Comparative Examples 1-2

Dental Compositions Containing Methacrylate Derivatives of C-8 Alcohol

Dental compositions containing methacrylate derivatives of C-8 Alcohol ("Hybrid" compounds) were prepared as follows: The photoinitiator components (e.g., CPQ, EDMAB, and DPIHFP) were initially dissolved in BisGMA by mechanically mixing the mixture in a glass jar for 3 hours at 55° C. The other components (including the filler) were then weighed in a MAX 20 plastic mixing cup having a screw cap (Flakteck, Landrum, S.C.). The cup was placed in an oven at 85° C. for 30 minutes. All of the components were then combined and mixed in a DAC 150 FV speed mixer (Flakteck) for 1 minute at 3000 rpm. Heating at 85° C. for 30 minutes and subsequent mixing were repeated twice. Dental compositions (Examples 5-9) were prepared in this manner as paste composites and the relative amounts of components for each composite are listed in Table 1. Comparative Examples 1 and 2 were prepared in a similar manner, except that the compositions contained the acetate (C-8 Acetate) and diurethane (C-8 diurethane) derivative of C-8 Alcohol in place of the "Hybrid" compounds (Table 1).

These composite pastes (Examples 5-9) were evaluated for diametral tensile strength (DTS), Watts shrinkage, Barcol hardness, and visual opacity according to the Test Methods described herein and the results compared to those from the commercial product 3M FILTEK SUPREME Universal Restorative (3M Company). Evaluation results are provided in Table 2. Comparative Examples 1 and 2 did not polymerize (i.e. harden) upon exposure to visible light (20 to 30 second exposure to visible light from an ELIPAR FreeLight Curing Light (3M Company)) and therefore no evaluation results were obtained.

It can be concluded from the results in Table 2 that the inventive dental composites (Examples 5-9) showed significantly improved shrinkage values in comparison with the commercial FILTEK SUPREME restorative product while maintaining good to excellent mechanical strength (DTS and Barcol Hardness values) and aesthetic (Visual Opacity values) properties.

TABLE 1

| Ingredient (Parts by Weight) | Dental Compositions | | | | | | |
|---|---|---|---|---|---|---|---|
| | Comp. Ex. 1 | Comp. Ex. 2 | Ex. 5 | Ex. 6 | Ex. 7 | Ex. 8 | Ex. 9 |
| BisGMA | 0 | 0 | 4.99 | 4.89 | 4.87 | 9.32 | 13.8 |
| BisEMA-6 | 0 | 0 | 4.35 | 4.32 | 0 | 0 | 0 |
| UDMA | 0 | 0 | 4.75 | 0 | 4.24 | 4.21 | 4.14 |
| Ex. 1 (Comp. A) | 0 | 0 | 9.50 | 9.49 | 13.54 | 9.12 | 4.73 |
| Ex. 2 (Comp. B) | 0 | 0 | 0 | 4.89 | 0 | 0 | 0 |
| C-8 Acetate | 98.36 | 0 | 0 | 0 | 0 | 0 | 0 |
| C-8 Diurethane | 0 | 98.36 | 0 | 0 | 0 | 0 | 0 |
| CPQ | 0.18 | 0.18 | 0.04 | 0.043 | 0.04 | 0.04 | 0.03 |
| EDMAB | 0.98 | 0.98 | 0.22 | 0.22 | 0.21 | 0.21 | 0.20 |

TABLE 1-continued

Dental Compositions

| Ingredient (Parts by Weight) | Comp. Ex. 1 | Comp. Ex. 2 | Ex. 5 | Ex. 6 | Ex. 7 | Ex. 8 | Ex. 9 |
|---|---|---|---|---|---|---|---|
| DPIHFP | 0.48 | 0.48 | 0.11 | 0.11 | 0.11 | 0.10 | 0.10 |
| BHT | 0 | 0 | 0.03 | 0.03 | 0 | 0 | 0 |
| Filler A | 0 | 0 | 76 | 76 | 77 | 77 | 77 |
| TOTAL: | 100 | 100 | 100 | 100 | 100 | 100 | 100 |

TABLE 2

Hardened Dental Compositions - Evaluation Results

| Example | Watts Shrinkage (%) | DTS MPa | Barcol Hardness Top | Barcol Hardness Bottom | Visual Opacity |
|---|---|---|---|---|---|
| 5 | 1.58 | 71 | 83 | 81 | 0.35 |
| 6 | 1.36 | 73 | 83 | 80 | 0.31 |
| 7 | 1.3 | 74 | 80 | 76 | 0.30 |
| 8 | 1.36 | 68 | 80 | 76 | 0.27 |
| 9 | 1.33 | 65 | 80 | 75 | NT* |
| FILTEK SUPREME | 1.93 | 76 | 86 | 85 | 0.35** |

*NT = Not Tested
**FILTEK SUPREME Restorative (unpigmented sample)

Examples 10-13

Dental Compositions Containing Methacrylate Derivatives of C-8 Alcohol

Dental compositions containing methacrylate derivatives of C-8 Alcohol ("Hybrid" compounds) were prepared as follows: The photoinitiator components (i.e., CPQ, EDMAB, and DPIHFP) were initially dissolved in the "Hybrid" compound by mechanically mixing the mixture in a glass jar. The filler was then added and all of the components mixed until the resulting paste became homogeneous. Dental compositions (Examples 10-13) were prepared in this manner as paste composites and the relative amounts of components for each composite are listed in Table 3.

These composite pastes (Examples 10-13) were evaluated for Barcol hardness according to the Test Method described herein and the results are provided in Table 4.

It can be concluded from the results in Table 4 that the inventive dental composites (Examples 10-13 each containing only a single "Hybrid" compound as the monomer resin) showed good to excellent Barcol Hardness values.

TABLE 3

Dental Compositions

| Ingredient (Parts by Weight) | Ex. 10 | Ex. 11 | Ex. 12 | Ex. 13 |
|---|---|---|---|---|
| Ex. 1 (Comp. A) | 0 | 0 | 0 | 23.58 |
| Ex. 2 (Comp. B) | 0 | 0 | 23.52 | 0 |
| Ex. 3A (Comp. C) | 23.58 | 0 | 0 | 0 |
| Ex. 3B (Comp. D) | 0 | 23.60 | 0 | 0 |
| CPQ | 0.04 | 0.04 | 0.05 | 0.04 |
| EDMAB | 0.25 | 0.23 | 0.24 | 0.24 |
| DPIHFP | 0.12 | 0.13 | 0.12 | 0.13 |
| Filler A | 76 | 76 | 76 | 76 |
| TOTAL: | 100 | 100 | 100 | 100 |

TABLE 4

Hardened Dental Compositions - Evaluation Results

| Example | Barcol Hardness Top | Barcol Hardness Bottom |
|---|---|---|
| 10 | 78 | 69 |
| 11 | 84 | 75 |
| 12 | 71 | 53 |
| 13 | 83 | 76 |

Examples 14-24

Dental Compositions Containing Methacrylate Derivatives of C-8 Alcohol

Dental compositions containing methacrylate derivatives of C-8 Alcohol ("Hybrid" compounds) were prepared as follows: The photoinitiator components (e.g., CPQ, EDMAB, DPIHFP, and I-819), methacrylate monomers, (BisGMA, BisEMA6, UDMA, and TEGDMA), and methacrylate derivatives of C-8 Alcohol were weighed in a MAX 20 plastic mixing cup having a screw cap (Flakteck). The cup was placed in an oven at 85° C. for 5 minutes, and then mixed in a DAC 150 FV speed mixer (Flakteck) for 1 minute at 3000 rpm. The filler component was then added and the cup was placed in an oven at 85° C. for 5 minutes and mixed in a DAC 150 FV speed mixer (Flakteck) for 1 minute at 3000 rpm. Heating at 85° C. for 5 minutes and subsequent mixing were repeated once. Dental compositions (Examples 14-24) were prepared in this manner as paste composites and the relative amounts of components for each composite are listed in Table 5.

These composite pastes (Examples 14-24) were evaluated for Watts shrinkage and Barcol hardness according to the Test Methods described herein and the results compared to those from the commercial product 3M FILTEK SUPREME Universal Restorative (3M Company). Evaluation results are provided in Table 6.

It can be concluded from the results in Table 4 that the inventive dental composites (Examples 14-24) showed generally improved shrinkage values in comparison with the commercial FILTEK SUPREME restorative product while generally maintaining good to excellent hardness (Barcol hardness values).

TABLE 5

Dental Compositions

| Ingredient (Parts by Weight) | Ex. 14 | Ex. 15 | Ex. 16 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|
| BisGMA | 5.68 | 5.69 | 5.67 | 5.46 | 5.46 | 5.44 | 2.87 | 2.87 | 2.86 |  | 2.87 |
| BisEMA-6 | 7.96 | 7.97 | 7.94 | 7.64 | 7.64 | 7.62 | 4.02 | 4.02 | 4.01 |  | 4.01 |
| UDMA | 7.96 | 7.97 | 7.94 | 7.64 | 7.64 | 7.62 | 4.02 | 4.02 | 4.01 |  | 4.01 |
| TEGDMA | 1.14 | 1.14 | 1.13 | 1.09 | 1.09 | 1.09 | 0.57 | 0.57 | 0.57 |  | 0.57 |
| Ex. 1 (Comp. A) | 0.24 | 0.24 | 0.24 | 1.16 | 1.16 | 1.16 | 11.48 | 11.49 | 11.45 |  |  |
| Ex. 3A (Comp. C) |  |  |  |  |  |  |  |  |  | 22.92 | 11.45 |
| CPQ | 0.04 |  | 0.04 | 0.04 |  | 0.04 | 0.04 |  | 0.04 | 0.04 | 0.04 |
| EDMAB |  | 0.24 |  |  | 0.24 |  |  |  | 0.24 | 0.24 | 0.24 |
| DPIHFP | 0.12 |  | 0.12 | 0.12 |  | 0.12 | 0.12 |  | 0.12 | 0.12 | 0.12 |
| I-819 |  | 0.08 |  |  | 0.08 |  |  | 0.06 |  |  |  |
| Filler A | 76.86 | 76.92 | 76.68 | 76.86 | 76.92 | 76.68 | 76.88 | 76.95 | 76.69 | 76.68 | 76.69 |
| TOTAL: | 100 | 100 | 100 | 100 | 100 | 100 | 100 | 100 | 100 | 100 | 100 |

TABLE 6

Hardened Dental Compositions - Evaluation Results

| Example | Watts Shrinkage (%) | Barcol Hardness Top | Barcol Hardness Bottom | Barcol Hardness* Top | Barcol Hardness* Bottom |
|---|---|---|---|---|---|
| 14 | 1.65 | 76 | 70 | 69 | 58 |
| 15 | 1.68 | 0 | 0 | 74 | 74 |
| 16 | 2.02 | 82 | 80 | 80 | 81 |
| 17 | 1.62 | 75 | 64 | 59 | 28 |
| 18 | 1.72 | 74 | 74 | 75 | 74 |
| 19 | 2.03 | 82 | 81 | 75 | 78 |
| 20 | 1.17 | 71 | 0 | 0 | 0 |
| 21 | 1.61 | 69 | 70 | 78 | 78 |
| 22 | 1.77 | 84 | 83 | 81 | 78 |
| 23 | 1.13 | 77 | 61 | NT** | NT |
| 24 | 1.76 | 86 | 82 | NT | NT |
| FILTEK SUPREME | 1.93 | 86 | 85 | NT | NT |

*Cured with VISILUX 2 Curing Light (3M Company)
**NT = Not Tested

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto.

The complete disclosures of the patents, patent documents, and publications cited herein are hereby incorporated by reference in their entirety as if each were individually incorporated.

What is claimed is:

1. A hardenable dental composition comprising a polymerizable compound having at least one cyclic allylic sulfide moiety with at least one (meth)acryloyl moiety attached thereto, wherein the compound comprises an oxygen atom directly bonded to the ring structure of the cyclic allylic sulfide moiety.

2. A hardenable dental composition comprising a polymerizable compound having at least one cyclic allylic sulfide moiety with at least one (meth)acryloyl moiety attached thereto, wherein the compound is represented by the formulae:

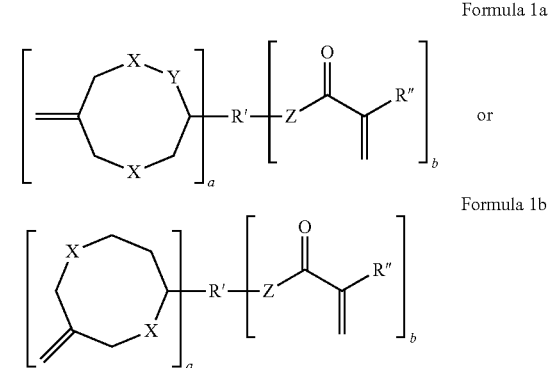

Formula 1a or Formula 1b wherein each X is independently selected from S, O, N, C, SO, $SO_2$, N-alkyl, N-acyl, NH, N-aryl, and carbonyl, provided that at least one X is S or a group comprising S;

Y is either absent or is a C1 to C3 alkylene, optionally including a heteroatom, carbonyl, acyl, or combinations thereof;

Z is O, NH, N-alkyl, or N-aryl;

R' is a linker comprising a group selected from alkylene with at least two carbons, alkylene having at least one heteroatom (e.g., O, N, S, S—S, SO, SO2), arylene, cycloaliphatic, carbonyl, siloxane, amido (—CO—NH—), acyl (—CO—O—), urethane (—O—CO—NH—), urea (—NH—CO—NH—) groups, and combinations thereof R" is H or $CH_3$;

a is 1 to 3; and b is 1 to 3;

wherein one or more of the cyclic allylic sulfide moieties can optionally be further substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group.

3. The composition of claim 1, wherein the cyclic allylic sulfide moiety contains two sulfur atoms.

4. The composition of claim 1 wherein the cyclic allylic sulfide moiety comprises an 8-membered ring.

5. The composition of claim 1 wherein the cyclic allylic sulfide moiety comprises a 7-membered ring.

6. The composition of claim 1 wherein the polymerizable compound has a MW of at least 250.

7. The composition of claim 1 wherein the (meth)acryloyl moiety comprises a (meth)acrylate or a (meth)acrylamide.

8. The composition of claim 1, further comprising an ethylenically unsaturated component.

9. The composition of claim 8, wherein the ethylenically unsaturated compound comprises a substituted (meth)acryloyl compound.

10. The composition of claim 9, wherein the substituted (meth)acryloyl compound comprises a di(meth)acrylate.

11. The composition of claim 9, where in, the substituted (meth)acryloyl compound comprises an aliphatic(meth)acrylate having at least one functional group.

12. The composition of claim 9, wherein the substituted (meth)acryloyl compound comprises a (meth)acrylate with an aromatic functionality.

13. The composition of claim 9, wherein the substituted (meth)acryloyl compound is selected from the group consisting of ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylgylcol dimethacrylate (NPGDMA), and polyethyleneglycol dimethacrylate (PEGDMA).

14. The composition of claim 3, wherein the composition further comprises an initiator system.

15. The composition of claim 14, wherein the initiator system comprises an electron donor, an iodonium salt, and a photosensitizer.

16. The composition of claim 14, wherein the initiator system comprises a phosphine oxide capable of absorbing light in the range of about 300 to about 600 nm.

17. The composition of claim 3, wherein the composition further comprises a filler.

18. The composition of claim 17, wherein the filler is surface modified with silane.

19. A method of preparing a dental restorative, the method comprising:
   providing a hardenable dental composition of claim 1;
   applying the composition to a tooth of a patient; and
   polymerizing the composition.

20. A compound represented by the following formulae:

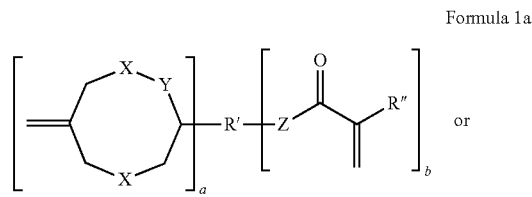

Formula 1a or

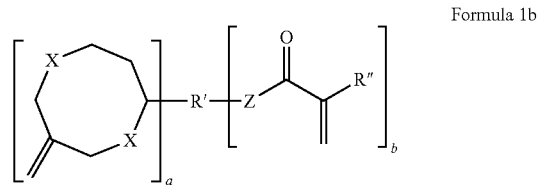

Formula 1b wherein each X is independently selected from S, O, N, C, SO, $SO_2$, N-alkyl, N-acyl, NH, N-aryl, and carbonyl, provided that at least one X is S or a group comprising S;

Y is either absent or is a C1 to C3 alkylene, optionally including a heteroatom, carbonyl, acyl, or combinations thereof;

Z is O, NH, N-alkyl, or N-aryl;

R' is a linker comprising a group selected from alkylene with at least two carbons, alkylene having at least one heteroatom (e.g., O, N, S, S—S, SO, SO2), arylene, cycloaliphatic, carbonyl, siloxane, amido (—CO—NH—), acyl (—CO—O—), urethane (—O—CO—NH—), urea (—NH—CO—NH—) groups, and combinations thereof R" is H or $CH_3$;

a is 1 to 3; and b is 1 to 3;

wherein one or more of the cyclic allylic sulfide moieties can optionally be further substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group.

* * * * *

UNITED STATES PATENT AND TRADEMARK OFFICE
CERTIFICATE OF CORRECTION

| | |
|---|---|
| PATENT NO. | : 7,888,400 B2 |
| APPLICATION NO. | : 11/912949 |
| DATED | : February 15, 2011 |
| INVENTOR(S) | : Ahmed S Abuelyaman |

It is certified that error appears in the above-identified patent and that said Letters Patent is hereby corrected as shown below:

On Page 2, in Column 2, under (Other Publications)
Line 14, delete "Sulfife" and insert -- Sulfide --, therefor.

IN THE SPECIFICATIONS:

Column 2
Line 4, delete "to" and insert -- two --, therefor.
Line 63, delete "akylthio," and insert -- alkylthio, --, therefor.

Column 3
Line 4, delete "akylthio," and insert -- alkylthio, --, therefor.
Line 28, delete "triethlyene" and insert -- triethylene --, therefor.
Line 29, delete "ethylenegylcol" and insert -- ethyleneglycol --, therefor.
Line 34, delete "photoinitator" and insert -- photoinitiator --, therefor.

Column 5
Line 43, delete "Marcomolecules," and insert -- Macromolecules, --, therefor.

Column 9
Line 2, delete "unsaturatd" and insert -- unsaturated --, therefor.
Line 17, delete "bisphenolA" and insert -- bisphenol A --, therefor.
Line 65, delete "triethlyene" and insert -- triethylene --, therefor.
Lines 66-67, delete "ethylenegylcol" and insert -- ethyleneglycol --, therefor.

Column 10
Line 57, delete "polyphosphonic" and insert -- polyphosphoric --, therefor.

Column 12
Line 12, delete "(2,6dimethoxybenzoyl)" and insert -- (2,6-dimethoxybenzoyl) --, therefor.

Signed and Sealed this
Twenty-seventh Day of September, 2011

David J. Kappos
*Director of the United States Patent and Trademark Office*

CERTIFICATE OF CORRECTION (continued)
U.S. Pat. No. 7,888,400 B2

Line 18, delete "1yl)" and insert -- 1-yl) --, therefor.
Line 49, delete "in" and insert -- nm --, therefor.

Column 13
Line 45, delete "(hydroxyethyl" and insert -- (hydroxyethyl) --, therefor.
Line 61, delete "hydropemxide," and insert -- hydroperoxide, --, therefor.

Column 14
Line 46, delete "unimodial" and insert -- unimodal --, therefor.
Line 46, delete "polymodial" and insert -- polymodal --, therefor.

Column 15
Line 4, delete "OSIL" and insert -- SIL --, therefor.

Column 19
Line 31, delete "37°C./90%+Relative" and insert -- 37°C./90%+ Relative --, therefor.

Columns 21-22, in (Table) (Including Structure)
Line 11, delete "Isocyanoatoethyl" and insert -- Isocyanatoethyl --, therefor.

Column 21
Line 47, delete "mmole)" and insert -- mmol) --, therefor.
Line 52, delete "mmole)" and insert -- mmol) --, therefor.

Column 22
Line 53, delete "mmole," and insert -- mmol, --, therefor.
Line 53, delete "mmole)" and insert -- mmol) --, therefor.

Column 23
Line 16, delete "-15-" and insert -- -1,5- --, therefor.
Line 33, delete "mmole)" and insert -- mmol) --, therefor.
Line 57, delete "dithiacyclooctan -3-yl)" and insert -- dithiacyclooctan-3-yl) --, therefor.

Column 24
Line 14, delete "1-(2-Acryloyloxyethyl)2" and insert -- 1-(2-Acryloyloxyethyl)-2 --, therefor.

IN THE CLAIMS:

Column 30
Line 66, in Claim 2, delete "akylthio," and insert -- alkylthio, --, therefor.

CERTIFICATE OF CORRECTION (continued)
U.S. Pat. No. 7,888,400 B2

Column 31
Line 17, in Claim 11, delete "where in," and insert -- wherein --, therefor.
Line 28, in Claim 13, delete "triethlyene" and insert -- triethylene --, therefor.
Line 29, in Claim 13, delete "ethylenegylcol" and insert -- ethyleneglycol --, therefor.
Line 30, in Claim 13, delete "neopentylgylcol" and insert -- neopentylglycol --, therefor.

Column 32
Line 44, in Claim 20, delete "akylthio," and insert -- alkylthio, --, therefor.